United States Patent
Stone et al.

(10) Patent No.: US 11,625,636 B2
(45) Date of Patent: Apr. 11, 2023

(54) SYSTEM AND METHOD FOR ORGANIC COGNITIVE RESPONSE (OCR) FEEDBACK FOR ADAPTIVE WORK INSTRUCTIONS

(71) Applicant: Raytheon Company, Waltham, MA (US)

(72) Inventors: Kristen M. Stone, Townsend, MA (US); James S. Neil, Groton, MA (US)

(73) Assignee: Raytheon Company, Waltham, MA (US)

(*) Notice: Subject to any disclaimer, the term of this patent is extended or adjusted under 35 U.S.C. 154(b) by 326 days.

(21) Appl. No.: 16/836,529

(22) Filed: Mar. 31, 2020

(65) Prior Publication Data
US 2021/0304048 A1    Sep. 30, 2021

(51) Int. Cl.
| | | |
|---|---|---|
| G06N 7/02 | (2006.01) | |
| G16H 40/67 | (2018.01) | |
| G16H 50/20 | (2018.01) | |
| G06F 9/451 | (2018.01) | |
| G06N 20/00 | (2019.01) | |
| A61B 5/18 | (2006.01) | |
| A61B 5/00 | (2006.01) | |
| G06Q 10/04 | (2012.01) | |
| G06Q 10/06 | (2012.01) | |
| G06Q 50/04 | (2012.01) | |
| G06Q 10/0631 | (2023.01) | |
| G06Q 10/0639 | (2023.01) | |

(52) U.S. Cl.
CPC ............ *G06N 7/02* (2013.01); *A61B 5/18* (2013.01); *A61B 5/7264* (2013.01); *G06F 9/451* (2018.02); *G06N 20/00* (2019.01); *G06Q 10/04* (2013.01); *G06Q 10/06316* (2013.01); *G06Q 10/06398* (2013.01); *G06Q 50/04* (2013.01); *G16H 40/67* (2018.01); *G16H 50/20* (2018.01)

(58) Field of Classification Search
None
See application file for complete search history.

(56) References Cited

U.S. PATENT DOCUMENTS 6,442,534 B1 * 8/2002 Au ................. G05B 13/0275
 706/3
9,360,340 B1 * 6/2016 Bailiang ............ G01C 21/367
(Continued)

FOREIGN PATENT DOCUMENTS

WO    2011/160222 A1    12/2011

OTHER PUBLICATIONS

Ruppert, Tamás, et al. "Enabling technologies for operator 4.0: A survey." Applied sciences 8.9 (2018): 1650 (Year: 2018).*
(Continued)

*Primary Examiner* — Darlene Garcia-Guerra (57) ABSTRACT

A method includes obtaining multiple inputs associated with a worker in a manufacturing environment. The method also includes performing a fuzzy logic process on the multiple inputs to generate multiple outputs, where the multiple outputs are associated with performance by the worker of a task in the manufacturing environment. The method further includes providing instructions to an electronic device to display a specified output among the multiple outputs while the worker performs the task in the manufacturing environment, where the specified output includes instruction information for performing the task.

20 Claims, 9 Drawing Sheets

(56) References Cited

U.S. PATENT DOCUMENTS

| | | | |
|---|---|---|---|
| 9,489,869 B2* | 11/2016 | Riojas | G09B 23/28 |
| 9,495,684 B2 | 11/2016 | Jung et al. | |
| 9,844,699 B2 | 12/2017 | Volkerink et al. | |
| 9,886,493 B2 | 2/2018 | Coleman et al. | |
| 10,475,351 B2* | 11/2019 | Horseman | G09B 9/00 |
| 10,556,600 B2 | 2/2020 | James | |
| 10,783,801 B1* | 9/2020 | Beaubien | A61B 5/0245 |
| 2010/0223212 A1* | 9/2010 | Manolescu | G09B 7/00 706/46 |
| 2013/0131507 A1* | 5/2013 | Salazar-Ferrer | A61B 6/5217 600/431 |
| 2013/0224709 A1* | 8/2013 | Riojas | G09B 23/28 434/262 |
| 2014/0247155 A1 | 9/2014 | Proud | |
| 2016/0132046 A1* | 5/2016 | Beoughter | G06F 16/248 700/17 |
| 2016/0244011 A1 | 8/2016 | Ricci | |
| 2017/0168703 A1* | 6/2017 | Feris | G06F 3/011 |
| 2017/0220956 A1* | 8/2017 | Stephens | G06F 3/0482 |
| 2017/0344919 A1 | 11/2017 | Chang et al. | |
| 2018/0028074 A1* | 2/2018 | Bertsch | A61B 5/1486 |
| 2018/0070823 A1 | 3/2018 | Blackwell et al. | |
| 2018/0268309 A1* | 9/2018 | Childress | G06F 40/237 |
| 2019/0107936 A1* | 4/2019 | Dunjic | G06Q 40/125 |
| 2019/0122036 A1 | 4/2019 | Ward et al. | |
| 2019/0224528 A1* | 7/2019 | Omid-Zohoor | A61B 5/0024 |
| 2019/0267002 A1* | 8/2019 | Crose | G10L 15/22 |
| 2019/0294719 A1 | 9/2019 | Beringer et al. | |
| 2019/0308639 A1 | 10/2019 | Ricci | |
| 2019/0346297 A1 | 11/2019 | Lekivetz et al. | |
| 2019/0369974 A1 | 12/2019 | Bequet et al. | |
| 2019/0373304 A1* | 12/2019 | Merjanian | H04N 21/431 |
| 2020/0043355 A1* | 2/2020 | Kwatra | G06Q 50/20 |
| 2020/0202472 A1* | 6/2020 | Barak | G06Q 10/0635 |
| 2020/0218335 A1* | 7/2020 | Soroker | G06F 3/167 |
| 2020/0265745 A1* | 8/2020 | Buras | G06N 20/00 |
| 2020/0274773 A1* | 8/2020 | Mortsolf | H04L 41/22 |
| 2020/0353312 A1* | 11/2020 | Smith | A63B 24/0075 |
| 2020/0387603 A1* | 12/2020 | Weldemariam | G06N 5/02 |
| 2021/0373664 A1* | 12/2021 | Duarte De Oliveira | G06F 3/0346 |

OTHER PUBLICATIONS

Syberfeldt, Anna, et al. "Dynamic operator instructions based on augmented reality and rule-based expert systems." Procedia Cirp 41 (2016): 346-351 (Year: 2016).*

Abraham, Ajith. "Rule-Based expert systems." Handbook of measuring system design (2005). (Year: 2005).*

Calderón, Juan M., and Luis G. Jaimes. "A fuzzy control-based approach for the selection of health interventions." 2018 15th IEEE Annual Consumer Communications & Networking Conference (CCNC). IEEE, 2018. (Year: 2018).*

Fragiadakis, N. G., V. D. Tsoukalas, and V. J. Papazoglou. "An adaptive neuro-fuzzy inference system (anfis) model for assessing occupational risk in the shipbuilding industry." Safety Science 63 (2014): 226-235 (Year: 2014).*

International Search Report and Written Opinion of the International Searching Authority dated Apr. 12, 2021 in connection with International Patent Application No. PCT/US2021/016922, 10 pages.

* cited by examiner

Assembly Instructions | Tech Company A | Revision A1

Parts List

| Part Number | Description | Qty |
|---|---|---|
| 456123-2 | SHCS 1/4 - 20 x 1 | 4 |
| 456117-1 | ASSEM BRACKET | 1 |
| 456899-3 | Mounting Base | 1 |
| 456888 | .5 IN Bolt | 1 |
| 456111 | .5 IN Nut | 1 |
| 456258 | Strut Brace | 1 |

Consumables

| Cage Code | Description |
|---|---|
| 57760 | Scotch Brite Pad (Red) |
| A8990 | Isopropyl Alcohol |
| LT2576 | Loctite 220 (red) |

Tools

| Tools |
|---|
| Torque Wrench 3/8" Drive |
| 1" Socket #/8" Drive |
| 1/4" Hex 3/8" Drive |
| 1" Combo Wrench |

Assembly Instructions

1. Locate the mounting block (456899-3) and prep the surface with an abrasive pad.
2. Clean the prepped surface with isopropyl alcohol and inspect for burrs or sharp edges.
3. Locate the mounting bracket (456117-1). Check the part for damage.
4. Install (456117-1) on (456899-3) using (QTY 4) 1/4 - 20 x 1" Socket Head Cap Screws.
5. Torque in an alternating pattern to a seating torque of 12 inlbs.
6. Repeat the pattern torqueing them to 24 inlbs and then again to 30 inlbs.
7. Locate the Strut Base (456258) and insert it into the mounting bracket (456117-1).
8. Locate the mounting hardware (QTY 1) 1/2 in X 2in Bolt and (QTY 1) .5in Nut and apply red Loctite per SOP H456777. Secure the strut using the hardware.
9. Torque Hardware to 40inlbs

Assembly Instructions | Tech Company A | Revision A1

STEP 1

| Designator | Part Number | Description | Qty |
|---|---|---|---|
| C | 456123-2 | SHCS 1/4 - 20 x 1 | 4 |
| B | 456117-1 | ASSEM BRACKET | 1 |
| A | 456899-3 | Mounting Base | 1 |

- Prep surface of A with Scotch Brite (S7760) and clean with isopropyl alcohol (A8990).
- Torque C in alternating pattern - 12, 24, and 30 inlbs

600

602

Text Only — Condensed Text and Picture — Expanded Text and Picture

SYSTEM AND METHOD FOR ORGANIC COGNITIVE RESPONSE (OCR) FEEDBACK FOR ADAPTIVE WORK INSTRUCTIONS

TECHNICAL FIELD

This disclosure is generally directed to machine learning systems. More specifically, this disclosure is directed to a system and method for organic cognitive response (OCR) feedback for adaptive work instructions.

BACKGROUND

Employees, such as shop floor workers in a manufacturing environment, are often required to be trained or instructed in tasks associated with their jobs. Example types of tasks can include cable routing, soldering, and the like. Such tasks can include a variety of skill types, including competence in the declarative, procedural, and psychomotor domains. Often times, procedures exist for training or instruction in such tasks. However, there may be little or no means for understanding and rectifying any gaps in the training or instruction procedures. These gaps may be due to a number of factors, such as deficiencies in cognitive functioning, aptitude, or abilities of each worker, deficiencies in the training or instruction procedures themselves, or a combination thereof.

SUMMARY

This disclosure relates to a system and method for organic cognitive response (OCR) feedback for adaptive work instructions.

In a first embodiment, a method includes obtaining multiple inputs associated with a worker in a manufacturing environment. The method also includes performing a fuzzy logic process on the multiple inputs to generate multiple outputs, where the multiple outputs are associated with performance by the worker of a task in the manufacturing environment. The method further includes providing instructions to an electronic device to display a specified output among the multiple outputs while the worker performs the task in the manufacturing environment, where the specified output includes instruction information for performing the task.

In a second embodiment, a system includes at least one memory configured to store instructions and at least one processor coupled to the at least one memory. The at least one processor is configured when executing the instructions to obtain multiple inputs associated with a worker in a manufacturing environment. The at least one processor is also configured when executing the instructions to perform a fuzzy logic process on the multiple inputs to generate multiple outputs, where the multiple outputs are associated with performance by the worker of a task in the manufacturing environment. The at least one processor is further configured when executing the instructions to provide instructions to an electronic device to display a specified output among the multiple outputs while the worker performs the task in the manufacturing environment, where the specified output includes instruction information for performing the task.

In a third embodiment, a non-transitory computer readable medium contains instructions that when executed cause at least one processor to obtain multiple inputs associated with a worker in a manufacturing environment. The non-transitory computer readable medium also contains instructions that when executed cause the at least one processor to perform a fuzzy logic process on the multiple inputs to generate multiple outputs, where the multiple outputs are associated with performance by the worker of a task in the manufacturing environment. The non-transitory computer readable medium further contains instructions that when executed cause the at least one processor to provide instructions to an electronic device to display a specified output among the multiple outputs while the worker performs the task in the manufacturing environment, where the specified output includes instruction information for performing the task.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 7, described below, and the various embodiments used to describe the principles of the present invention in this patent document are by way of illustration only and should not be construed in any way to limit the scope of the invention. Those skilled in the art will understand that the principles of the present invention may be implemented in any type of suitably arranged device or system.

As noted above, manufacturing employees are often required to be trained or instructed in tasks associated with their jobs. As used here, "training" generally refers to information learned before performing a task, and "instructions" generally refer to information referenced while performing a task. While procedures may exist for training or instruction in such tasks, there may be little or no means for understanding and rectifying any gaps in the training or instruction procedures. One existing procedure is a "Gemba walk," which allows managers or leaders to observe actual work process, engage with employees, gain knowledge about the work processes, and explore opportunities for continuous improvement. However, the Gemba walk is a manual process that does not automatically generate feedback. Another procedure or process is a "time study," which is a structured process of directly observing and measuring human work using a timing device to establish the time required for completion of the work by a qualified worker when working at a defined level of performance. However, time studies generate very limited results. Currently, little or nothing exists in the manufacturing space that integrates empirical data of wearable sensors and human factor data collection to provide feedback for dynamically changing task instructions according to the feedback.

This disclosure provides systems and methods for measuring and using organic cognitive response (OCR) feedback for adaptive work instructions. As used here, "organic cognitive response" and "OCR" refer to the way that people respond and adapt to information (such as training information or instructions) that they are provided. As described in more detail below, the disclosed systems and methods use information that is collected from sensors, cognitive assessment techniques, and other sources and applies the information to provide a feedback mechanism for workers that perform their jobs with standardized work instructions in a manufacturing setting, such as on a production floor. The collected information can be used to adapt the instructions to be more individualized and more suitable for each worker, even though the instructions have standardized information. The collected information can also be used to detect burnout, fatigue, or other problems with workers who may be weary from performing the same activities repeatedly. Note that while the disclosed embodiments are described in the context of a manufacturing setting, it will be understood that the principles of this disclosure can be incorporated into any skills training or instruction environment.

Figure 1:
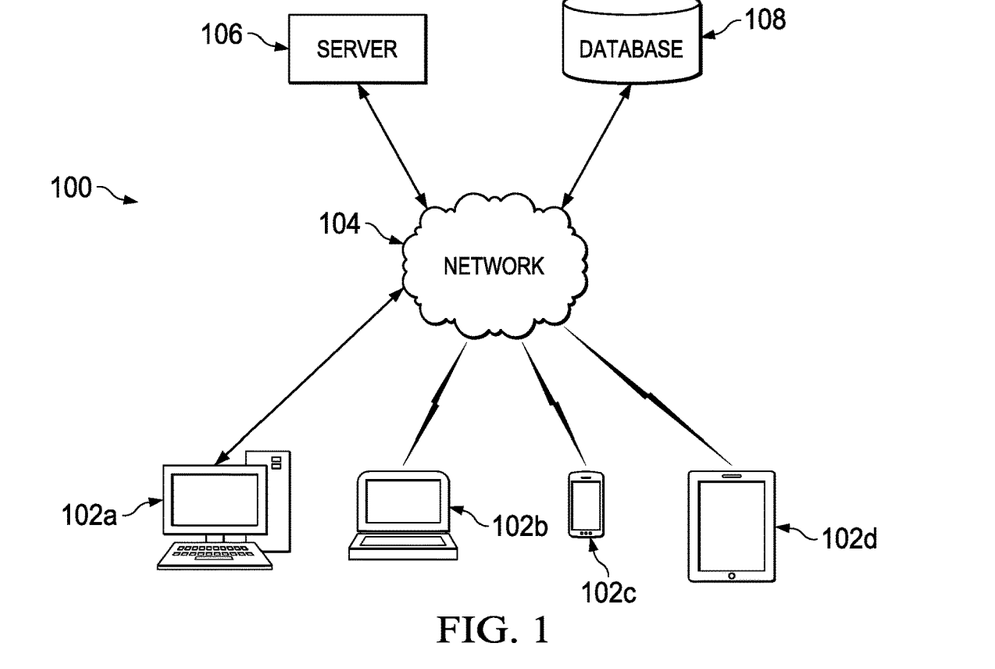
FIG. 1 illustrates an example system for measuring and using organic cognitive response (OCR) feedback for adaptive work instructions according to this disclosure.

FIG. 1 illustrates an example system 100 for measuring and using OCR feedback for adaptive work instructions according to this disclosure. As shown in FIG. 1, the system 100 includes multiple user devices 102a-102d, at least one network 104, at least one server 106, and at least one database 108. Note, however, that other combinations and arrangements of components may also be used here.

In this example, each user device 102a-102d is coupled to or communicates over the network 104. Communications between or involving each user device 102a-102d and the network 104 may occur in any suitable manner, such as via a wired or wireless connection. Each user device 102a-102d represents any suitable device or system used by at least one user to provide information to the server 106 or database 108 or to receive information from the server 106 or database 108. Example types of information may include cognitive assessment information, sensor data, training information, and the like. Any suitable number(s) and type(s) of user devices 102a-102d may be used in the system 100. In this particular example, the user device 102a represents a desktop computer, the user device 102b represents a laptop computer, the user device 102c represents a smartphone, and the user device 102d represents a tablet computer. However, any other or additional types of user devices may be used in the system 100, such as smart glasses, smart watches, wearable sensors, fitness trackers, and the like. Each user device 102a-102d includes any suitable structure configured to transmit and/or receive information.

The network 104 facilitates communication between various components of the system 100. For example, the network 104 may communicate Internet Protocol (IP) packets, frame relay frames, Asynchronous Transfer Mode (ATM) cells, or other suitable information between network addresses. The network 104 may include one or more local area networks (LANs), metropolitan area networks (MANs), wide area networks (WANs), all or a portion of a global network such as the Internet, or any other communication system or systems at one or more locations. The network 104 may also operate according to any appropriate communication protocol or protocols.

The server 106 is coupled to the network 104 and is coupled to or otherwise communicates with the database 108. The server 106 supports the retrieval of information from the database 108 and the processing of that information. Of course, the database 108 may also be used within the server 106 to store information, in which case the server 106 may store the information itself. Among other things, the server 106 processes information for measuring and using OCR feedback for adaptive work instructions. The server 106 includes any suitable structure configured to process OCR feedback information for adaptive work instructions. In some embodiments, the server 106 includes one or more processors, one or more memories, and one or more communication interfaces. Note, however, that the server 106 may be implemented in any suitable manner to perform the described functions. Also note that while described as a server here, the device(s) actually implementing the server 106 may represent one or more desktop computers, laptop computers, server computers, or other computing or data processing devices or systems.

The database 108 stores various information used, generated, or collected by the server 106 and the user devices 102a-102d. For example, the database 108 may store cognitive assessment information, sensor data, training information, and the like. The database 108 may support any suitable technique for storing and retrieving information.

Note that there are a number of possible ways to implement the system 100 in order to provide the described functionality for measuring and using OCR feedback for adaptive work instructions. For example, in some embodiments, the server 106 and database 108 are owned, operated, or managed by a common entity. In other embodiments, the server 106 and database 108 are owned, operated, or managed by different entities. However, this disclosure is not limited to any particular organizational implementation.

Although FIG. 1 illustrates one example of a system 100 for measuring and using OCR feedback for adaptive work instructions, various changes may be made to FIG. 1. For example, the system 100 may include any number of user devices 102a-102d, networks 104, servers 106, and databases 108. Also, while FIG. 1 illustrates that one database 108 is coupled to the network 104, any number of databases 108 may reside at any location or locations accessible by the server 106, and each database 108 may be coupled directly or indirectly to the server 106. In addition, while FIG. 1 illustrates one example operational environment in which OCR feedback can be measured and used for adaptive work instructions, this functionality may be used in any other suitable system.

Figure 2:
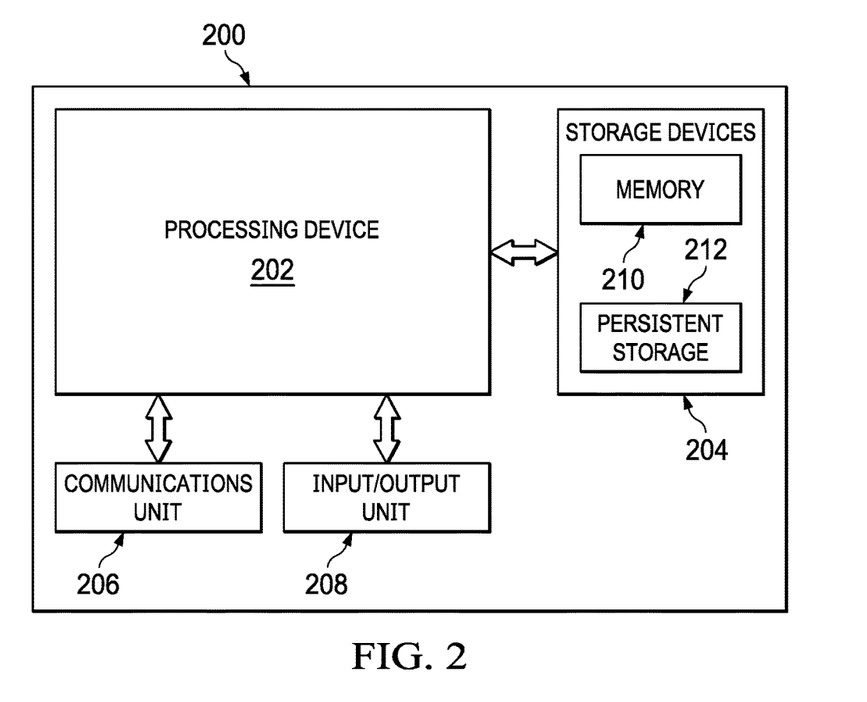
FIG. 2 illustrates an example device for measuring and using OCR feedback for adaptive work instructions according to this disclosure.

FIG. 2 illustrates an example device 200 for measuring and using OCR feedback for adaptive work instructions according to this disclosure. One or more instances of the device 200 may, for example, be used to at least partially implement the functionality of the server 106 of FIG. 1. However, the functionality of the server 106 may be implemented in any other suitable manner. Also, the same or similar arrangement of components may be used to at least partially implement the functionality of one or more of the user devices 102a-102d in FIG. 1. However, the functionality of each user device 102a-102d may be implemented in any other suitable manner.

As shown in FIG. 2, the device 200 denotes a computing device or system that includes at least one processing device 202, at least one storage device 204, at least one communications unit 206, and at least one input/output (I/O) unit 208. The processing device 202 may execute instructions that can be loaded into a memory 210. The processing device 202 includes any suitable number(s) and type(s) of processors or other devices in any suitable arrangement. Example types of processing devices 202 include one or more microprocessors, microcontrollers, digital signal processors (DSPs), application specific integrated circuits (ASICs), field programmable gate arrays (FPGAs), or discrete circuitry.

The memory 210 and a persistent storage 212 are examples of storage devices 204, which represent any structure(s) capable of storing and facilitating retrieval of information (such as data, program code, and/or other suitable information on a temporary or permanent basis). The memory 210 may represent a random access memory or any other suitable volatile or non-volatile storage device(s). The persistent storage 212 may contain one or more components or devices supporting longer-term storage of data, such as a read only memory, hard drive, Flash memory, or optical disc.

The communications unit 206 supports communications with other systems or devices. For example, the communications unit 206 can include a network interface card or a wireless transceiver facilitating communications over a wired or wireless network, such as the network 104. The communications unit 206 may support communications through any suitable physical or wireless communication link(s).

The I/O unit 208 allows for input and output of data. For example, the I/O unit 208 may provide a connection for user input through a keyboard, mouse, keypad, touchscreen, or other suitable input device. The I/O unit 208 may also send output to a display, printer, or other suitable output device. Note, however, that the I/O unit 208 may be omitted if the device 200 does not require local I/O, such as when the device 200 can be accessed remotely.

In some embodiments, the instructions executed by the processing device 202 can include instructions that implement the functionality of the server 106 described above. For example, the instructions executed by the processing device 202 can include instructions for measuring and using OCR feedback for adaptive work instructions.

Although FIG. 2 illustrates one example of a device 200 for measuring and using OCR feedback for adaptive work instructions, various changes may be made to FIG. 2. For example, computing devices and systems come in a wide variety of configurations, and FIG. 2 does not limit this disclosure to any particular computing device or system.

Figure 3:
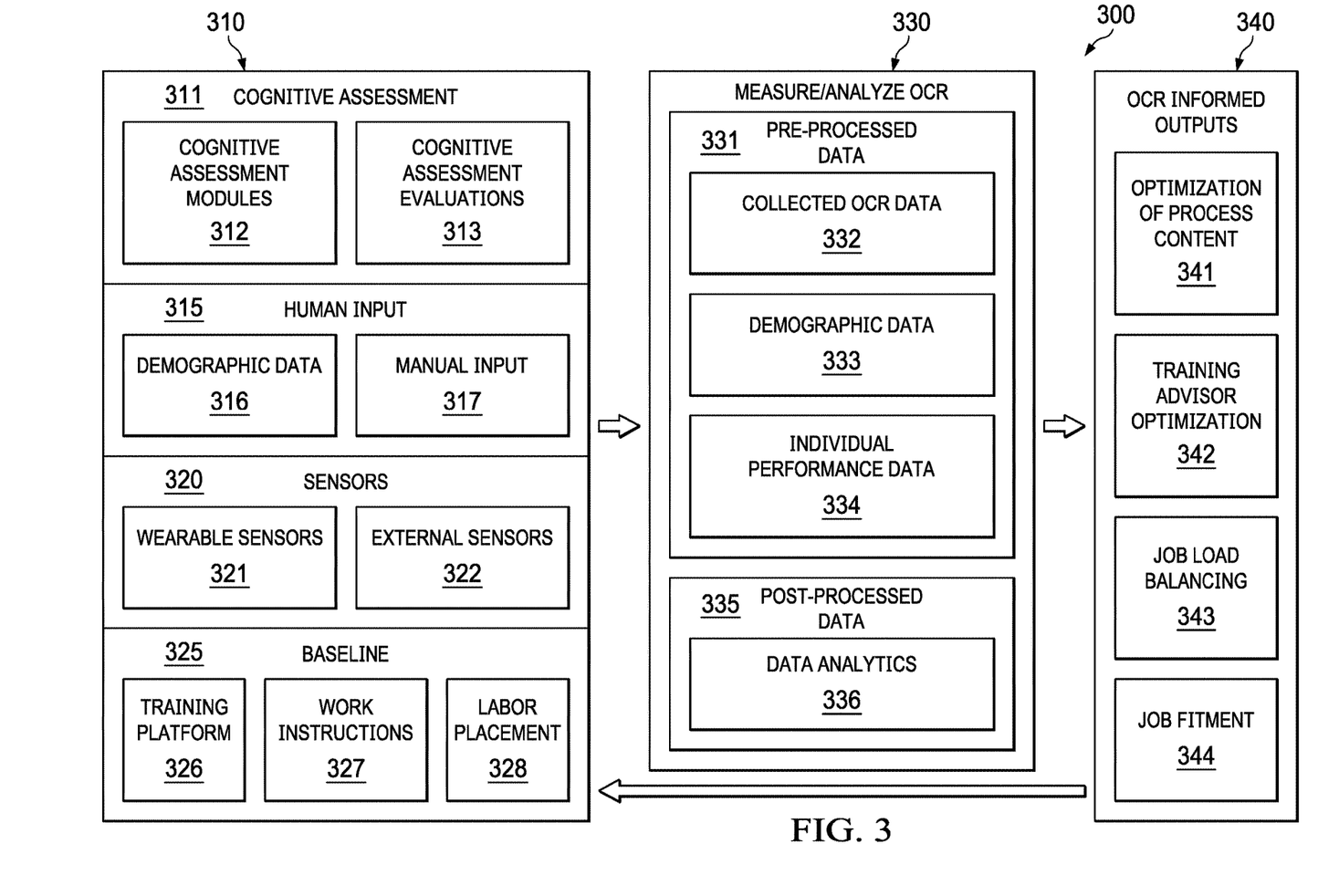
FIG. 3 illustrates an example process for measuring and using OCR feedback for adaptive work instructions according to this disclosure.

FIG. 3 illustrates an example process 300 for measuring and using OCR feedback for adaptive work instructions according to this disclosure. For ease of explanation, the process 300 of FIG. 3 may be described as being performed by the server 106 of FIG. 1, which may be implemented using the device 200 of FIG. 2. However, the process 300 may involve the use of any suitable device(s) in any suitable system(s).

As shown in FIG. 3, the process 300 includes the receipt of multiple process inputs 310, which are collected and provided as inputs to various process operations 330. Upon execution, the process operations 330 generate multiple process outputs 340, some of which can be fed back to update or improve the process inputs 310.

The process inputs 310 include a diverse group of information that can be used for measuring and using OCR feedback for adaptive work instructions. As described below, the process inputs 310 can be collected at different times using different input methods. The process inputs 310 can be stored in one or more databases, such as the database 108, for retrieval by the process operations 330. For ease of explanation, the process inputs 310 are generally organized into multiple categories here. However, the categories are not rigidly defined, and some input information may relate to more than one category.

One category of process input 310 is cognitive assessment information 311. Cognitive assessment information 311 includes information that is generated as a result of one or more cognitive assessments that are performed on a worker. The cognitive assessments can take different forms. In some embodiments, each worker interacts with one or more cognitive assessment modules 312, which are computer-based applications that are executed (such as on a workstation, tablet, or mobile phone) to determine health or acute cognitive ability information about the worker. In particular embodiments, each cognitive assessment module 312 is presented as a short game or quiz that is designed to be enjoyable for the worker. For example, one cognitive assessment module 312 may test a worker's reaction by instructing the worker to tap a symbol on a touch screen display as soon as the symbol appears. Another cognitive assessment module 312 may instruct the worker to arrange a group of numbers in order as quickly as possible. Yet another cognitive assessment module 312 may instruct the worker to distinguish between cartoon-like "alien" creatures based on differences in appearance.

Each cognitive assessment modules 312 can be designed to be completed quickly by the worker, such as within a couple of minutes or less. Each worker may be requested to complete one or more cognitive assessment modules 312 at the start of each work shift, at multiple times throughout the workday, whenever worker fatigue is detected, or according to any other suitable schedule or at any other suitable times. Whenever a worker completes a cognitive assessment module 312, the results can be stored in a database (such as the database 108) for later use by the process operations 330.

The cognitive assessments can also include one or more cognitive assessment evaluations 313. Each cognitive assessment evaluation 313 can be performed by each worker and can include questions or mental exercises designed to evaluate the worker's cognitive functions and suitability for work tasks. In some embodiments, a cognitive assessment evaluation 313 can be configured like a questionnaire and can include questions such as "How exciting/enjoyable is your current workload?" or "Are there certain times in the day when you feel more engaged with your job?" The cognitive assessment evaluations 313 are typically completed by each worker less frequently than the cognitive assessment modules 312. For example, a worker may complete each cognitive assessment evaluation 313 at the start of employment, once a year, when a worker performance issue is identified, or according to any other suitable schedule or at any other suitable times. Whenever a worker completes a cognitive assessment evaluation 313, the results can be stored in a database (such as the database 108) for later use by the process operations 330.

Another category of process input 310 is human input information 315. Human input information 315 includes demographic data 316 of the worker and manual inputs 317 by the worker. The demographic data 316 can include demographic information such as age, gender, height, weight, work experience, health conditions, eye prescriptions, and the like. The demographic data 316 can be input by the worker (or by another person on the worker's behalf) at the start of employment, at the start of a new employment position, or according to any other suitable schedule or at any other suitable times. Once collected, the demographic data 316 can be stored in a database (such as the database 108) for later use by the process operations 330.

The manual inputs 317 can include information or operations that are input or performed by a worker while the worker is performing a work task, which may (among other things) be used to enable a change to the worker's environment. One example of a manual input 317 is a worker actuating a control in an electronically-presented set of work instructions. The worker can actuate the control (such as by moving a slider element on a slider control in a graphical user interface or "GUI") to change the presentation of the work instructions in a way that is preferable to the worker. When the worker performs one or more manual inputs 317, information can be collected and stored about what manual inputs 317 are performed by the worker, when the manual inputs 317 are performed, and what other events or activities are occurring when the manual inputs 317 are performed in order to draw correlations between the manual input 317, current conditions, and desired outcomes.

Figure 4A:
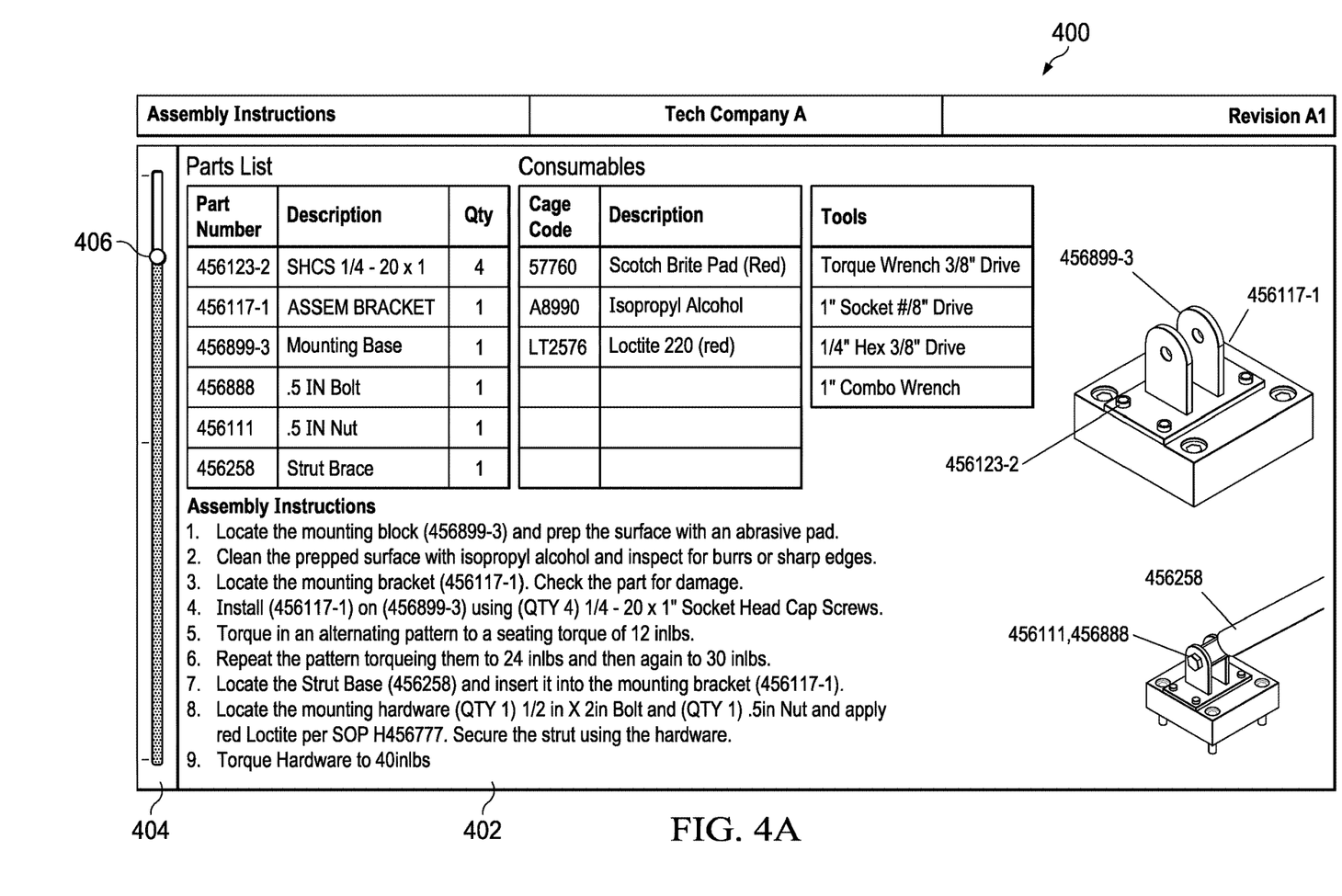
FIGS. 4A and 4B illustrate different views of an example user interface in which a worker can provide a manual input according to this disclosure.
Figure 4B:
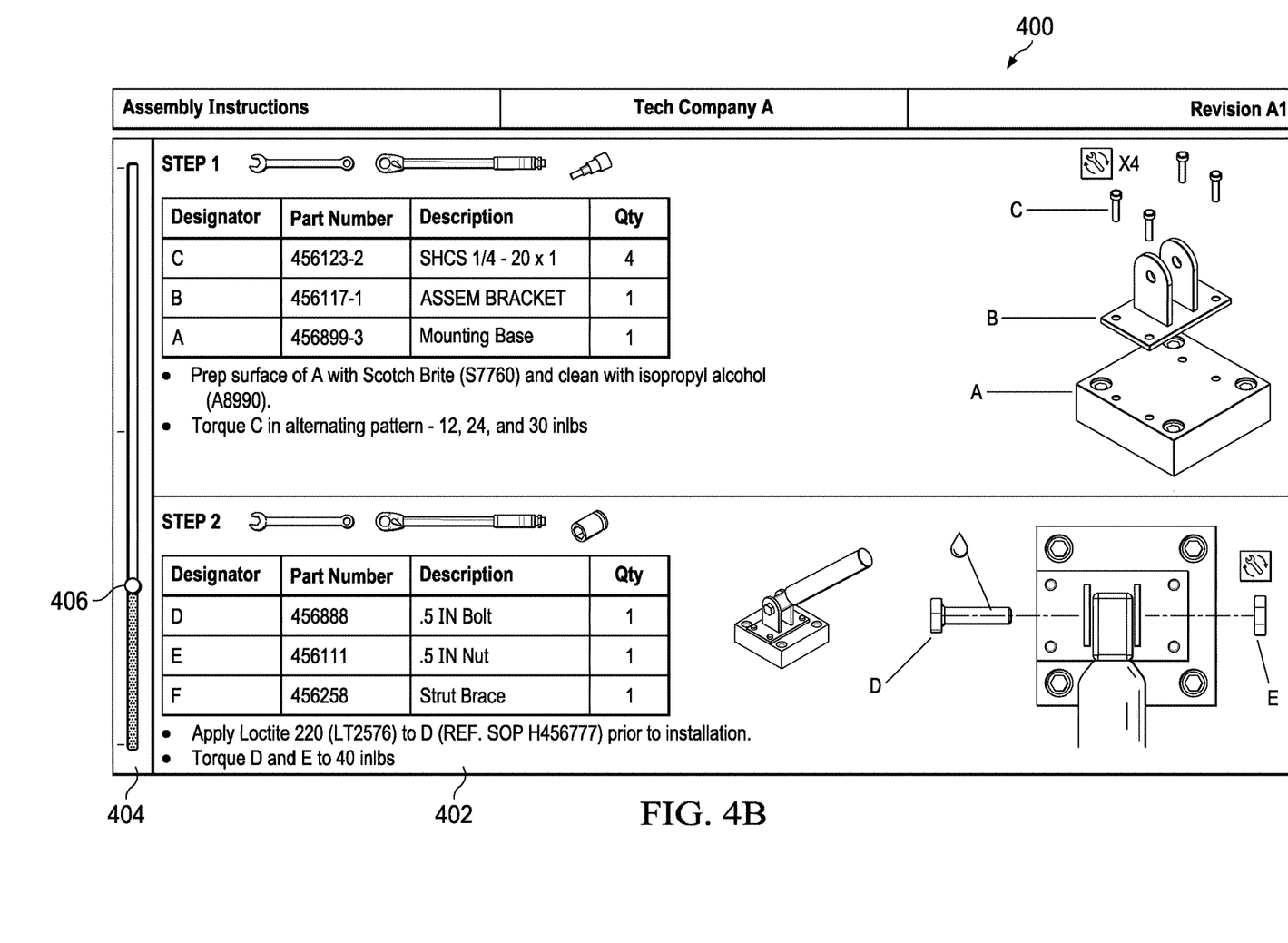

There are various ways in which manual inputs 317 may be obtained from a user. FIGS. 4A and 4B illustrate different views of an example user interface 400 in which a worker can provide a manual input 317 according to this disclosure. For ease of explanation, the user interface 400 is described as being shown on a display of one of the user devices 102a-102d. However, the user interface 400 may involve the use of any suitable device(s) in any suitable system(s).

As shown in FIGS. 4A and 4B, the user interface 400 includes an instruction information section 402 and a control section 404. The instruction information section 402 shows information associated with instructions for performing a manufacturing-related task. Most manufacturing facilities have a standardized, pre-approved set of work instructions to perform each manufacturing task, such as assembly of a component or inspection of a product. In many cases, the instructions are provided to be followed by each worker and are uniform so that all workers follow the same instructions to perform the same tasks. In some complex assembly tasks, the number of steps can number in the hundreds or thousands, so reference by the worker to the instructions is often critical to success.

However, different workers receive and process instruction information differently, have different levels of experience and existing knowledge, work at different paces, etc. Thus, the control section 404 includes a user control 406 that allows the worker to provide a manual input 317 for controlling the display of information in the instruction information section 402. The user control 406 can be actuated by the worker (such as by sliding the user control 406 up or down) to allow the worker to select a level of information that is most helpful for that worker.

In FIG. 4A, a worker has moved the user control 406 to a higher position. In response to the higher position, the user interface 400 shows instruction information at an increased level in the instruction information section 402. That is, the instruction information section 402 shows relatively more detail, which here includes multiple figures and many types of information densely arranged in the instruction information section 402. This level of information may be overwhelming for some workers, which can cause the worker to stop work or ignore a step.

In contrast, in FIG. 4B, the worker has moved the user control 406 to a lower position. In response, the user interface 400 shows instruction information at a reduced level in the instruction information section 402. That is, the instruction information section 402 shows relatively less detail, which here includes fewer figures and fewer or simpler words in the text. This level of information may be more easily understood by some workers, but other workers (such as more experienced workers) may find this level of information too simple.

The overall instructions for performing a task are substantially the same at each level of detail. Thus, if the instruction information section 402 shows less detail in a single image, a user may need to review multiple images to receive all of the instructions for a task. However, the way the information is presented in the instruction information section 402 can be changed in various ways. Example changes can include more or less information on a single screen; different colored text, font, or font size; arrangement of information on a screen (such as text above images, text below images, or text superimposed on images), and the like. These changes can help a specific worker interpret the information in the most suitable way for that worker.

Although FIGS. 4A and 4B illustrate different views of an example user interface 400 in which a worker can provide a manual input, various changes may be made to FIGS. 4A and 4B. For example, manufacturing instructions can include a wide variety of information presented as text, images, drawings, diagrams and the like, and these figures do not limit the scope of this disclosure.

Turning again to FIG. 3, another category of process input 310 is sensor information 320. Sensor information 320 can include information that is generated by one or more sensors operating in the environment where the worker performs his or her job. In some embodiments, the sensor information 320 includes wearable sensor information 321 and external sensor information 322.

Wearable sensor information 321 includes information generated by one or more sensors worn by the worker, such as smart glasses, a smart watch, a fitness tracker, or the like. Wearable sensor information 321 is typically information that is directly associated with the worker, such as the worker's body temperature, pulse, blood pressure, posture or position (like standing, sitting, etc.), speed or direction of worker movement, and the like. The wearable sensor information 321 can be continuously or intermittently collected while the worker performs tasks associated with the worker's job and transmitted in real-time or non-real-time to a database (such as the database 108) for storage. Once collected, this type of worker information can be used in the process 300 to correlate the worker's current health status or position with operations the worker performs while working.

External sensor information 322 includes information generated by sensors that are in the worker's environment (such as in the vicinity of the worker) but that are not directly worn by the worker. Such sensors can include environmental sensors for detecting and measuring room temperature, light, noise, and the like; machine sensors for measuring product or process parameters (machine speed, tank pressure, material quantities or throughputs, etc.), and any other suitable sensors for measuring conditions in the worker's external environment. The external sensor information 322 can be continuously or intermittently collected while the worker performs tasks associated with the worker's job and transmitted in real-time or non-real-time to a database (such as the database 108) for storage. Some external sensor information 322 (especially light and noise levels) can directly affect the worker's current physical, emotional, or mental state (which may be detected and collected as wearable sensor information 321) and may therefore play a significant role in how the worker reacts to training or instructions.

Another category of process input 310 is baseline deliverable information 325. Baseline deliverable information 325 is a broad category of information that can be used as both an input and an output in the process 300. In some embodiments, the baseline deliverable information 325 includes training platform information 326, work instruction information 327, and labor placement information 328.

The training platform information 326 includes information that can used in any kind of worker training, such as soldering training, safety training, sexual harassment training, ethics training, and the like. The training platform information 326 can include training instruction materials that are used for instruction during training, training assessment materials (such as tests, quizzes, worker test results, etc.) that indicate a worker's performance after training, and the like.

The work instruction information 327 includes instruction information that the worker uses during performance of his or her job. In particular, the work instruction information 327 can include the actual set of process instructions that are followed while the worker actively performs a job task on the factory floor. For example, the text and diagram information shown in the instruction information section 402 of FIGS. 4A and 4B are examples of work instruction information 327.

Labor placement information 328 includes information related to the worker's work environment and tasks where the worker is assigned. For example, labor placement information 328 can indicate if the work task is a mentally or physically challenging task. Labor placement information 328 can also indicate if the work environment is a dirty work environment, a hazardous environment, or a low-light environment.

The various types of baseline deliverable information 325 can be used as inputs to inform the process 300, and results from the process 300 can be used to update or revise the baseline deliverable information 325. For example, training platform information 326 may indicate that a worker is very inexperienced with a particular work task. Once this training platform information 326 is input to the process 300, the process operations 330 may generate an output indicating that certain work instruction information 327 should be presented at a very elementary level so that the inexperienced worker can follow the instructions.

The process operations 330 obtain one or more of the process inputs 310, which are also referred to as pre-processed data 331 in the process operations 330. The pre-processed data 331 can include OCR data 332, demographic data 333, and individual worker performance data 334, where each can represent different combinations or subsets of the process inputs 310. Various combinations of the pre-processed data 331 can be used during each execution of the process operations 330.

The process operations 330 are executed (such as by the server 106) to generate post-processed data 335, which can include data analytics 336, as described in greater detail below. The post-processed data 335 can be collected and stored in a database (such as the database 108) to be used as one or more of the process outputs 340. Various combinations of the process outputs 340 can be generated as a result of the execution of the process operations 330. For example, the process outputs 340 can include information associated with optimizing a worker's environment, training, instruction sets, or health so that the worker is able to perform his or her work tasks efficiently, accurately, and in a positive manner.

The process operations 330 include one or more machine learning or data analytics algorithms, such as fuzzy logic. Fuzzy logic is a type of artificial intelligence that uses "fuzzy" (vague or imprecisely-defined) classes to determine relationships and connections over time and to make predictions about future behaviors. Fuzzy logic is well-suited for problem solving in many types of control systems, industrial systems, and manufacturing environments. In contrast to binary logic where variables are represented only as zeros and ones, each variable in fuzzy logic can have a value that ranges in degree (such as anywhere between zero and one). Fuzzy logic systems can use a membership function, such as a graph that represents a magnitude of the degree of membership of each input variable (like each process input 310) that is in the interval between zero and one. The degree of membership of a variable x can be denoted by the symbol $\mu(x)$.

Figure 5A:
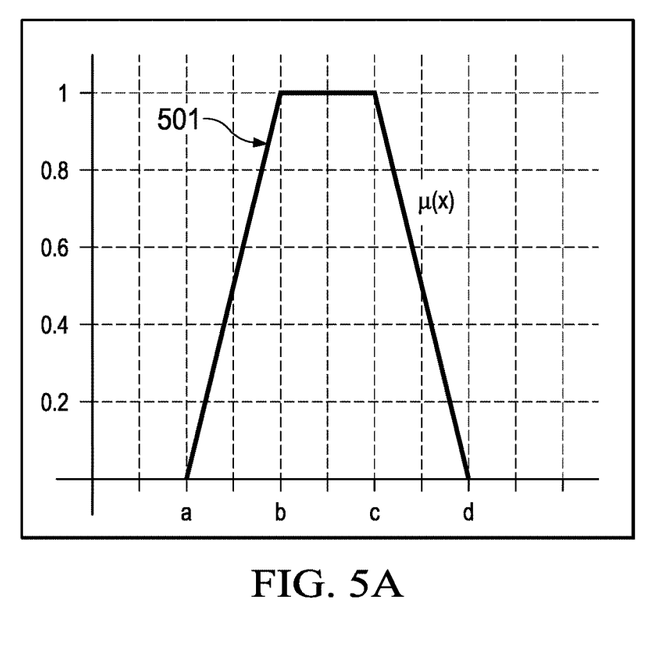
FIGS. 5A and 5B illustrate example functions that may be used in the process of FIG. 3 according to this disclosure.
Figure 5B:
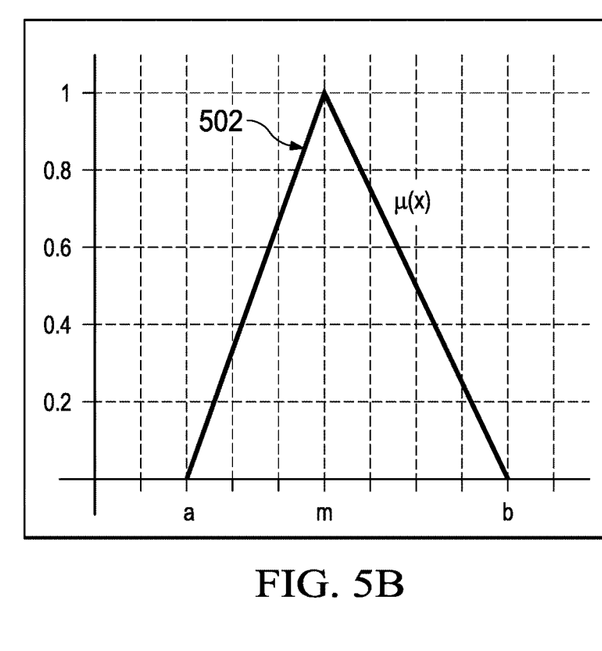

In some embodiments, the process operations 330 can include implementation of a Mamdani fuzzy inference system. Mamdani fuzzy inference systems convert each input variable into one of multiple types of membership functions, including triangular, trapezoidal, singleton, sigmoid, and Gaussian functions and the like. FIGS. 5A and 5B illustrate example functions 501 and 502 that may be used in the process of FIG. 3 according to this disclosure. In particular, FIG. 5A illustrates an example of a trapezoidal function 501 in which $\mu(x)$ is defined by a lower limit a, an upper limit d, a lower support limit b, and an upper support limit c, where $a<b<c<d$. FIG. 5B illustrates an example of a triangular function 502 in which $\mu(x)$ is defined by a lower limit a, an upper limit b, and a value m, where $a<m<b$.

The process outputs 340 represent results or findings that are generated by execution of the process operations 330. As discussed above, the process outputs 340 include information associated with optimizing conditions associated with a worker, such as the worker's environment, training, instruction sets, or health. In particular, the process outputs 340 can include predictive information (such as worker cognitive workload or burden) that anticipates when a worker may fail at a task or when environmental conditions are likely to cause a failure, so that corrective measures can be implemented. For ease of explanation, the process outputs 340 are generally organized into multiple categories. However, the categories are not rigidly defined, and some output information may relate to more than one category.

One category of process outputs 340 is optimization information 341. Optimization information 341 includes information related to optimizing the type and amount of instruction information provided to a worker when the worker performs a work-related task. One example of optimization information is a customized default setting for the user control 406 and a customized level of information for the instruction information section 402 of FIGS. 4A and 4B. Over time, the process operations 330 can learn through feedback what is most helpful for a particular worker in a particular environment (which can include time of day or day of week, in addition to physical environment) for that type of task and preselect a level of detail when presenting the instructions. As a particular example, the process operations 330 may determine that a worker is very inexperienced with a particular work task. Thus, the process operations 330 may generate optimization information 341 for automatically causing the instruction information section 402 to present instructions at a very elementary level so that the inexperienced worker can easily follow the instructions. This can promote worker success and worker satisfaction. The worker can accept the preselected level or override by moving the user control 406. Whenever the worker manually overrides by moving the user control 406, that represents a new process input 310 that the process operations 330 can later use to refine the feedback.

Another category of process outputs 340 is training advisor information 342. Training advisor information 342 can be used to understand which training is more effective and which is less effective for each worker so that the training can be optimized or customized for each worker or group of workers. For example, the process operations 330 may identify trends (through collected data analytics 336) and determine that multiple workers are performing poorly on one type of task, even though the workers have been trained for that task. Since multiple workers are performing poorly (rather than just one or two workers), the training advisor information 342 may include a conclusion that the training itself is deficient and a recommendation to improve the training platform information 326 for that task.

Additional categories of output information include job load balancing information 343 and job fitment information 344. Job load balancing information 343 relates to whether or not the right number of workers are in each job or whether some workers should be reassigned. Job fitment information 344 relates to whether or not each worker is fit (such as suitably skilled, trained, and physically able) for the job to which the worker is currently assigned. An example of job fitment information 344 can include a notification predicting when a worker may be about to fail in operations, thus causing rework. The notification can be generated as a result of the process operations 330 determining that the worker's blood pressure or heart rate usually increases when the worker is performing certain tasks or is working at certain times of the day or that the worker tends to skip the same steps during a particular process. Thus, the job fitment information 344 may include a recommendation that the worker be relieved from that task, a break be scheduled, or the like.

Although FIG. 3 illustrates one example of a process 300 for measuring and using OCR feedback for adaptive work instructions, various changes may be made to FIG. 3. For example, various operations in FIG. 3 may overlap, occur in parallel, occur in a different order, or occur any number of times.

Figure 6A:
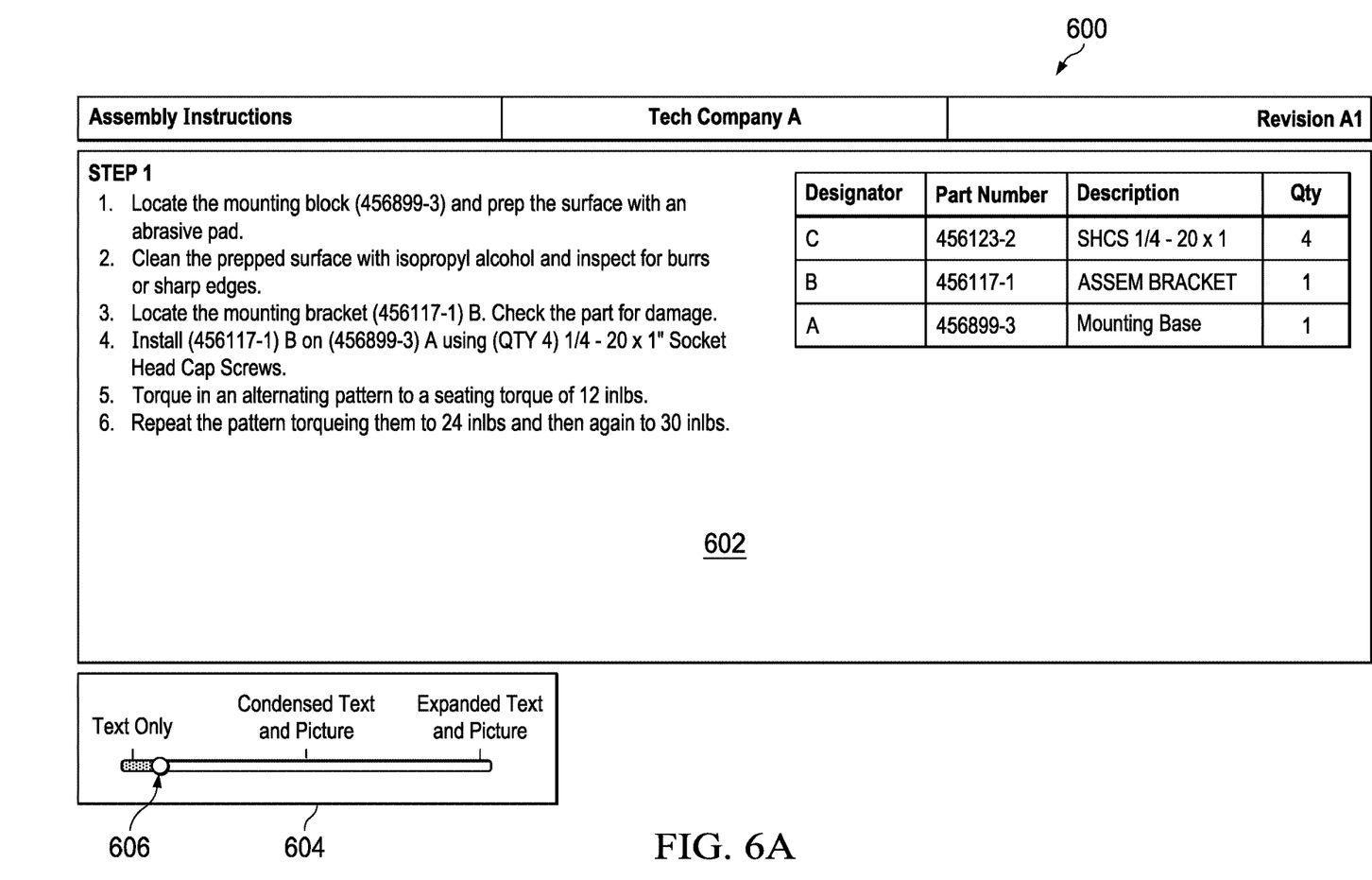
FIGS. 6A through 6C illustrate different views of another example user interface in which a worker can provide a manual input according to this disclosure.
Figure 6B:
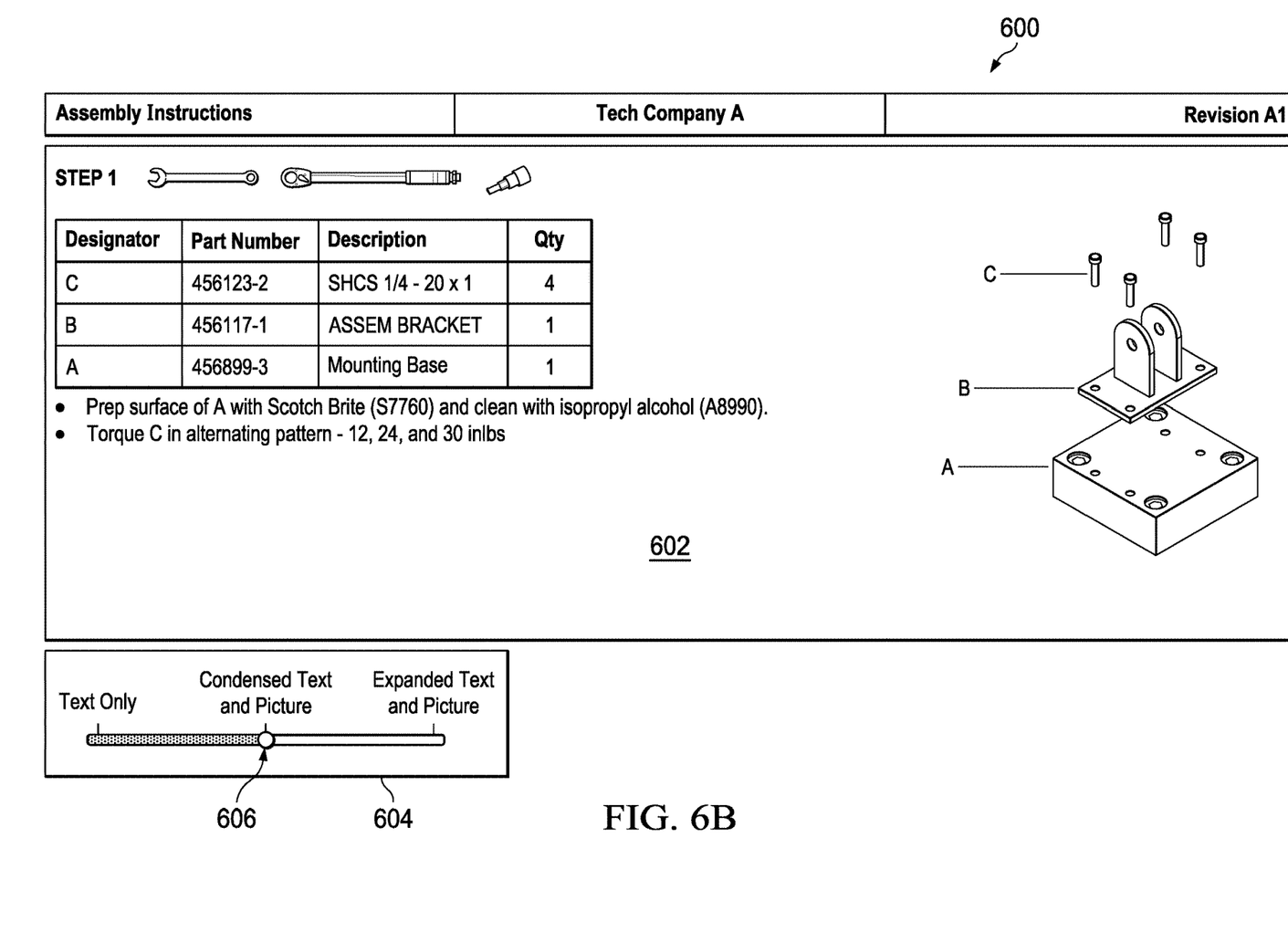
Figure 6C:
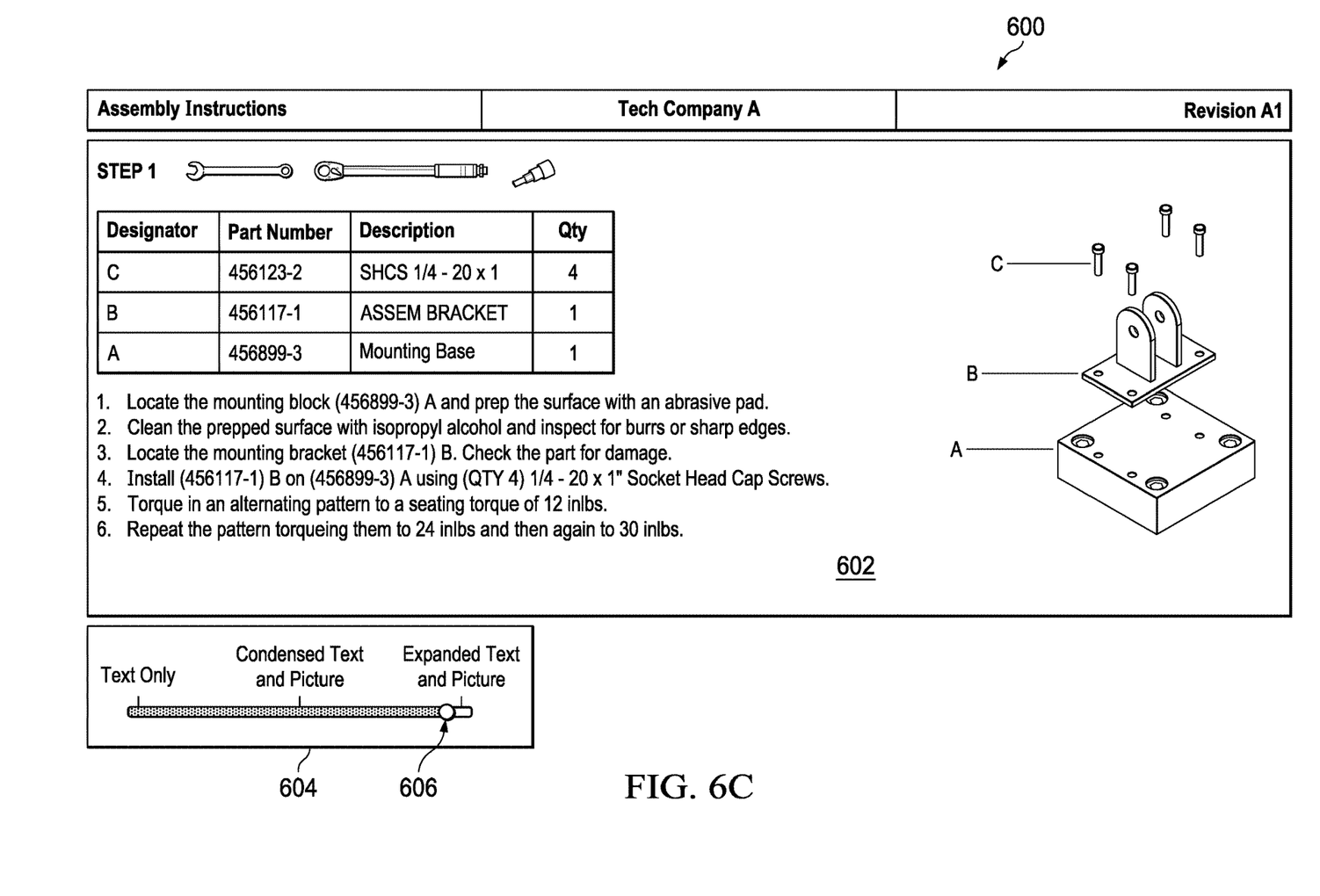

FIGS. 6A through 6C illustrate different views of another example user interface 600 in which a worker can provide a manual input according to this disclosure. For ease of explanation, the user interface 600 is described as being shown on a display of one of the user devices 102a-102d. However, the user interface 600 may involve the use of any suitable device(s) in any suitable system(s).

As shown in FIGS. 6A through 6C, the user interface 600 includes an instruction information section 602 and a control section 604 that includes a user control 606. The user control 606 allows the worker to change visibility states of the work instructions (such as color, text, images, CAD models, etc.) in the instruction information section 602, which enables the worker to perform tasks using a preferred informational theme. In FIG. 6A, the user control 606 is moved to a "Text Only" position, and as a result the instruction information section 602 shows only text instructions. In FIG. 6B, the user control 606 is moved to a "Condensed Text and Picture" position, and as a result the instruction information section 602 shows some text and one or more pictures. In FIG. 6C, the user control 606 is moved to an "Expanded Text and Picture" position, and as a result the instruction information section 602 shows additional text and pictures.

In some embodiments, actuation of the user control 606 or another user control can toggle visibility (such as between revealed and hidden visibility states) or otherwise toggle the functionality of other controls or components, such as touch screen buttons. In addition, in some embodiments, actuation of the user control 606 or another user control can result in a change to the colors of the background or fonts that are shown in the instruction information section 602. This can be helpful for workers who experience eye strain or are colorblind or who work in environments that have differing levels of background illumination. In particular embodiments, the user preferences can be collected and stored in a data table (such as in the database 108) and retrieved when a worker logs into an instruction workstation using his or her own login credentials. The login can automatically bring up a content view that is specialized for that worker.

Although FIGS. 6A through 6C illustrate different views of another example user interface 600 in which a worker can provide a manual input, various changes may be made to FIGS. 6A through 6C. For example, manufacturing instructions can include a wide variety of information presented as text, images, drawings, diagrams and the like, and these figures do not limit the scope of this disclosure.

Figure 7:
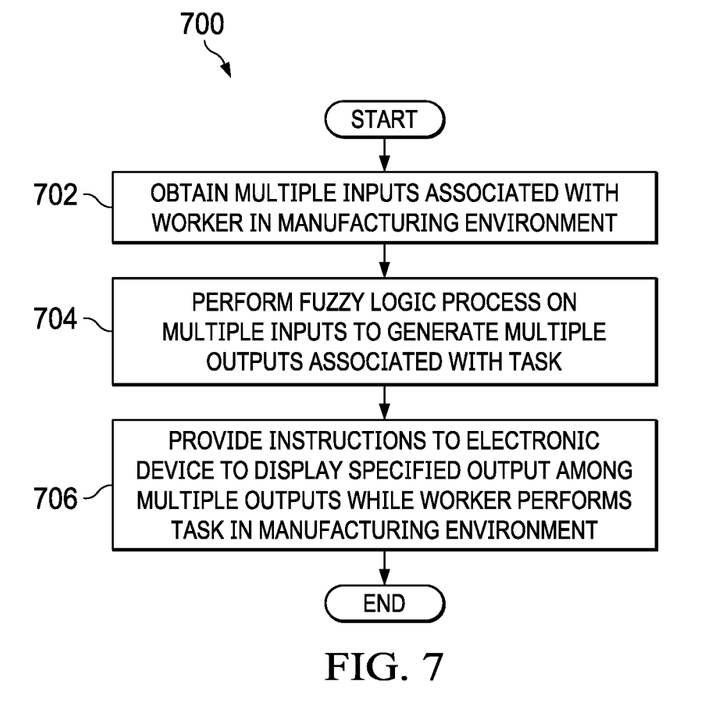
FIG. 7 illustrates an example method for measuring and using OCR feedback for adaptive work instructions according to this disclosure.

FIG. 7 illustrates an example method 700 for measuring and using OCR feedback for adaptive work instructions according to this disclosure. For ease of explanation, the method 700 of FIG. 7 may be described as being performed by the server 106 of FIG. 1 (which may be implemented using the device 200 of FIG. 2) using the process 300 in FIG. 3. However, the method 700 may involve the use of any suitable device(s) and process(es) in any suitable system(s).

As shown in FIG. 7, multiple inputs associated with a worker in a manufacturing environment are obtained at step 702. This may include, for example, the server 106 obtaining multiple process inputs 310 that are stored in a database 108, transmitted from one or more sensors, or from any other suitable location. In some embodiments, the multiple inputs can include sensor information generated by at least one sensor worn by the worker (such as wearable sensor information 321) while the worker performs a task, sensor information generated by at least one sensor located in a vicinity of the worker (such as external sensor information 322) while the worker performs the task, or a combination of these. In some embodiments, the multiple inputs can include cognitive assessment information associated with a cognitive assessment of the worker, such as cognitive assessment information 311.

A fuzzy logic process is performed on the multiple inputs to generate multiple outputs at step 704. The multiple outputs are associated with performance by the worker of the task in the manufacturing environment. This may include, for example, the server 106 performing the process operations 330, which can include a fuzzy logic process, to generate multiple process outputs 340. In some embodiments, the multiple outputs 340 can include job load balancing information, job fitment information, or both.

Instructions are provided to an electronic device to display a specified output among the multiple outputs while the worker performs the task in the manufacturing environment at step 706. The specified output includes instruction information for performing the task. This may include, for example, the server 106 providing instructions to an electronic device used by the worker so that the electronic device displays instruction information for performing the task. The instruction information for performing the task can be optimized for the worker using the fuzzy logic process. In some embodiments, the specified output also includes a user control that allows the worker to control a detail level of the instruction information that is displayed on the electronic device.

Although FIG. 7 illustrates one example of a method 700 for measuring and using OCR feedback for adaptive work instructions, various changes may be made to FIG. 7. For example, while shown as a series of steps, various steps in FIG. 7 may overlap, occur in parallel, occur in a different order, or occur any number of times.

In some embodiments, various functions described in this patent document are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable storage device.

It may be advantageous to set forth definitions of certain words and phrases used throughout this patent document. The terms "application" and "program" refer to one or more computer programs, software components, sets of instructions, procedures, functions, objects, classes, instances, related data, or a portion thereof adapted for implementation in a suitable computer code (including source code, object code, or executable code). The term "communicate," as well as derivatives thereof, encompasses both direct and indirect communication. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," or "controller" within a claim is understood and intended to refer to structures known to those skilled in the relevant art, as further modified or enhanced by the features of the claims themselves, and is not intended to invoke 35 U.S.C. § 112(f).

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
obtaining multiple inputs associated with a worker in a manufacturing environment;
performing a fuzzy logic process on the multiple inputs to generate multiple outputs, the multiple outputs associated with performance by the worker of a task in the manufacturing environment, wherein a specified output of the multiple outputs generated by the fuzzy logic process comprises (i) a first default setting indicating a detail level of instruction information for performing the task and (ii) a second default setting indicating a position of a user control of a user interface, wherein performing the fuzzy logic process comprises implementing a Mamdani fuzzy inference system on the multiple inputs to generate the first default setting and the second default setting; and
providing instructions to an electronic device to display the specified output while the worker performs the task in the manufacturing environment, the specified output also comprising the instruction information for performing the task, the instruction information initially presented according to the first default setting, the specified output further comprising the user control, the user control configured to adjustably control the detail level of the instruction information based on the position of the user control selected by the worker, wherein an initial setting of the user control is set according to the second default setting.

2. The method of claim 1, wherein the multiple inputs comprise at least one of:
first sensor information generated by a first sensor worn by the worker while the worker performs the task; and
second sensor information generated by a second sensor located in a vicinity of the worker while the worker performs the task.

3. The method of claim 1, wherein the multiple inputs comprise cognitive assessment information associated with a cognitive assessment of the worker.

4. The method of claim 1, wherein the instruction information for performing the task is optimized for the worker using the fuzzy logic process.

5. The method of claim 1, wherein the multiple outputs further comprise at least one of job load balancing information and job fitment information.

6. The method of claim 1, wherein:
the worker is one of multiple workers in the manufacturing environment; and
at least one of the multiple inputs or the multiple outputs is associated with training of the multiple workers.

7. The method of claim 1, wherein the multiple inputs comprise demographic data of the worker.

8. A system comprising:
at least one memory configured to store instructions; and
at least one processor coupled to the at least one memory and configured when executing the instructions to:

obtain multiple inputs associated with a worker in a manufacturing environment;

perform a fuzzy logic process on the multiple inputs to generate multiple outputs, the multiple outputs associated with performance by the worker of a task in the manufacturing environment, wherein a specified output of the multiple outputs generated by the fuzzy logic process comprises (i) a first default setting indicating a detail level of instruction information for performing the task and (ii) a second default setting indicating a position of a user control of a user interface, wherein, to perform the fuzzy logic process, the at least one processor is configured to implement a Mamdani fuzzy inference system on the multiple inputs to generate the first default setting and the second default setting; and provide instructions to an electronic device to display the specified output while the worker performs the task in the manufacturing environment, the specified output also comprising the instruction information for performing the task, the instruction information initially presented according to the first default setting, the specified output further comprising the user control, the user control configured to adjustably control the detail level of the instruction information based on the position of the user control selected by the worker, wherein an initial setting of the user control is set according to the second default setting.

9. The system of claim 8, wherein the multiple inputs comprise at least one of:
first sensor information generated by a first sensor worn by the worker while the worker performs the task; and
second sensor information generated by a second sensor located in a vicinity of the worker while the worker performs the task.

10. The system of claim 8, wherein the multiple inputs comprise cognitive assessment information associated with a cognitive assessment of the worker.

11. The system of claim 8, wherein the at least one processor is configured to use the fuzzy logic process to optimize the instruction information for performing the task for the worker.

12. The system of claim 8, wherein the multiple outputs further comprise at least one of job load balancing information and job fitment information.

13. The system of claim 8, wherein the worker is one of multiple workers in the manufacturing environment and at least one of the multiple inputs or the multiple outputs is associated with training of the multiple workers.

14. The system of claim 8, wherein the multiple inputs comprise demographic data of the worker.

15. A non-transitory computer readable medium containing instructions that when executed cause at least one processor to:

obtain multiple inputs associated with a worker in a manufacturing environment;

perform a fuzzy logic process on the multiple inputs to generate multiple outputs, the multiple outputs associated with performance by the worker of a task in the manufacturing environment, wherein a specified output of the multiple outputs generated by the fuzzy logic process comprises (i) a first default setting indicating a detail level of instruction information for performing the task and (ii) a second default setting indicating a position of a user control of a user interface, wherein, to perform the fuzzy logic process, the at least one processor is configured to implement a Mamdani fuzzy inference system on the multiple inputs to generate the first default setting and the second default setting; and provide instructions to an electronic device to display the specified output while the worker performs the task in the manufacturing environment, the specified output also comprising the instruction information for performing the task, the instruction information initially presented according to the first default setting, the specified output further comprising the user control, the user control configured to adjustably control the detail level of the instruction information based on the position of the user control selected by the worker, wherein an initial setting of the user control is set according to the second default setting.

16. The non-transitory computer readable medium of claim 15, wherein the multiple inputs comprise at least one of:
first sensor information generated by a first sensor worn by the worker while the worker performs the task; and
second sensor information generated by a second sensor located in a vicinity of the worker while the worker performs the task.

17. The non-transitory computer readable medium of claim 15, wherein the multiple inputs comprise cognitive assessment information associated with a cognitive assessment of the worker.

18. The non-transitory computer readable medium of claim 15, wherein the instructions when executed cause the at least one processor to use the fuzzy logic process to optimize the instruction information for performing the task for the worker.

19. The non-transitory computer readable medium of claim 15, wherein the multiple outputs further comprise at least one of job load balancing information and job fitment information.

20. The non-transitory computer readable medium of claim 15, wherein the multiple inputs comprise demographic data of the worker.

* * * * *